United States Patent
Thomas et al.

(10) Patent No.: US 10,307,120 B1
(45) Date of Patent: Jun. 4, 2019

(54) VERTICAL MOVING HORIZONTAL APERTURE RING POSITRON EMISSION TOMOGRAPHY SCANNER AND CHAIR WITH STATIONARY CYCLE FOR STRESSING THE PATIENT'S HEART

(71) Applicants: Paul B. Thomas, San Pedro, CA (US); Farhad Daghighian, Santa Monica, CA (US)

(72) Inventors: Paul B. Thomas, San Pedro, CA (US); Farhad Daghighian, Santa Monica, CA (US)

(73) Assignee: Prescient Imaging, LLC, Hawthorne, CA (US)

(*) Notice: Subject to any disclaimer, the term of this patent is extended or adjusted under 35 U.S.C. 154(b) by 73 days.

(21) Appl. No.: 15/420,069

(22) Filed: Jan. 30, 2017

Related U.S. Application Data

(60) Provisional application No. 62/384,697, filed on Sep. 7, 2016.

(51) Int. Cl.
*A61B 6/03* (2006.01)
*A61B 6/00* (2006.01)

(52) U.S. Cl.
CPC ............ *A61B 6/4435* (2013.01); *A61B 6/037* (2013.01); *A61B 6/4266* (2013.01); *A61B 6/465* (2013.01)

(58) Field of Classification Search
CPC ......... A61B 6/04; A61B 6/037; A61B 6/0478; A61B 6/032; A61B 6/44
See application file for complete search history.

(56) References Cited

U.S. PATENT DOCUMENTS

| | | | | |
|---|---|---|---|---|
| 4,316,091 | A * | 2/1982 | Bernardi | A61B 6/4429 378/17 |
| 5,042,487 | A * | 8/1991 | Marquardt | A61B 6/0457 378/17 |
| 6,735,274 | B1 * | 5/2004 | Zahavi | A61B 6/032 378/15 |
| 8,055,325 | B1 * | 11/2011 | Damadian | A61B 5/0555 5/601 |
| 2005/0138731 | A1 * | 6/2005 | Failor | A61G 5/006 5/601 |
| 2014/0265500 | A1 * | 9/2014 | Hough | A61G 5/14 297/340 |
| 2014/0378829 | A1 * | 12/2014 | Soluri | A61B 6/03 600/425 |
| 2015/0208992 | A1 * | 7/2015 | Marash | A61B 6/4476 600/427 |
| 2017/0071561 | A1 * | 3/2017 | Bernhardt | A61N 5/1049 |

* cited by examiner

*Primary Examiner* — Yara B Green
(74) *Attorney, Agent, or Firm* — Jerry Fong

(57) ABSTRACT

A positron emission tomography (PET) scanner in which a horizontal detector ring is arranged to be moved vertically up and down by a lifting mechanism, thereby eliminating the need for a patient to be in a supine position when performing PET or other types of image scanning.

11 Claims, 8 Drawing Sheets

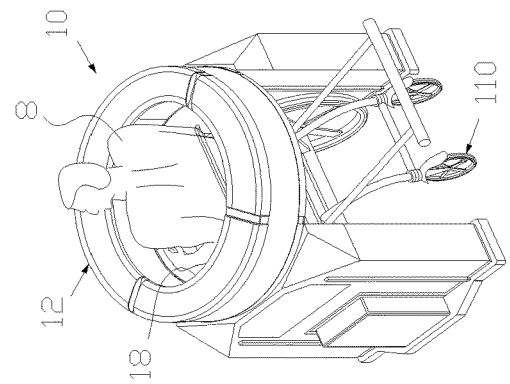
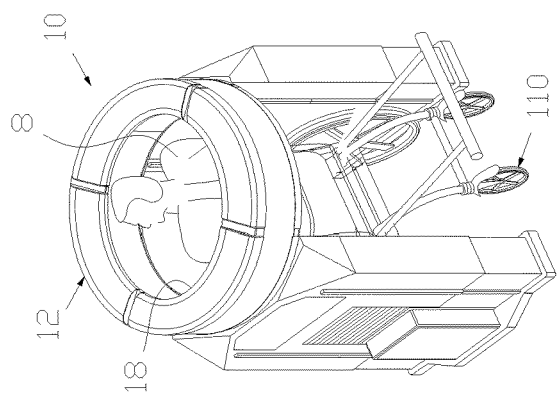
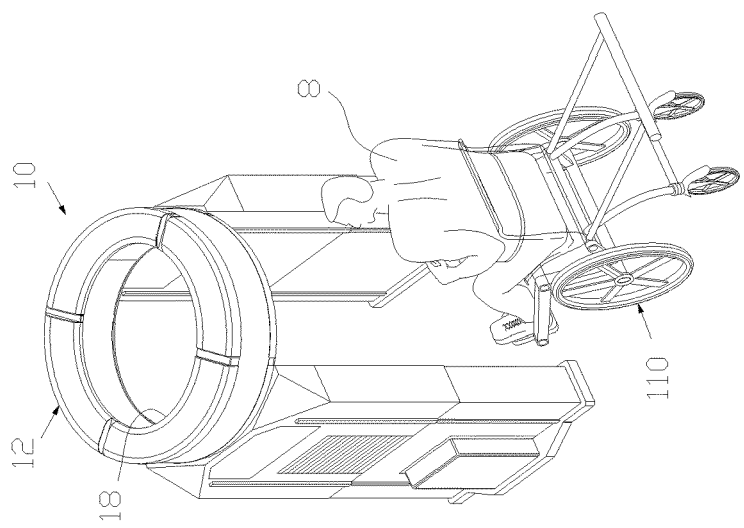

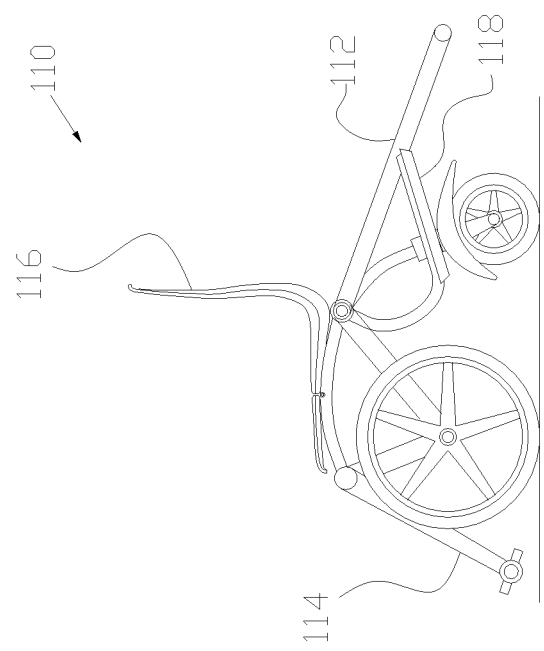

VERTICAL MOVING HORIZONTAL APERTURE RING POSITRON EMISSION TOMOGRAPHY SCANNER AND CHAIR WITH STATIONARY CYCLE FOR STRESSING THE PATIENT'S HEART

BACKGROUND OF THE INVENTION

1. Field of the Invention

The present invention generally relates to medical imaging systems. More particularly, the present invention relates to a vertical-moving horizontal ring PET scanner.

2. Description of the Prior Art

Medical imaging technology has made remarkable advances over the years including developments and improvements on positron emission tomography (PET). The use of PET has grown in the field of medical imaging. PET has gained attention as being effective in making an early diagnosis of cancers, heart diseases, cerebrovascular disorders, dementia and others. PET is an imaging method that relies on injecting IV, a compound labeled with a trace amount of a positron emitting nuclide. The PET's detector ring identify paired photons (511 keV of energy each) produced by the positron annihilation effect. The paired 511 keV photons travel in the opposite direction at a 180° angle from each other. Therefore, positron decay can be localized without collimation, as used for SPECT, but with the use of the principle of coincidence detection. As PET cameras do not necessitate collimators, these systems have a much higher sensitivity than do SPECT cameras. PET scan is a map of radioactive concentration in various tissues based on the specific biochemical properties of the tracer. For example, metabolism of glucose or blood flow in heart muscle (myocardium), and examining the presence or absence of a disease and the seriousness of a disease, and prognoses during the course of therapy. For the implementation thereof, PET scanners have been put into practical use. Another advantage of PET vs. SPECT is its capability to measure the radioactive concentration inside the body without the disturbing effect of tissue attenuation.

PET-myocardial perfusion imaging (MPI) allows accurate measurement of myocardial perfusion, absolute myocardial blood flow and function at stress and rest in a single study session performed in approximately 30 minutes. Various PET tracers are available for MPI and rubidium-82 or nitrogen-13-ammonia is most commonly used. Relative quantification of PET perfusion images shows very high diagnostic accuracy for detection of obstructive coronary artery disease. Dynamic myocardial blood flow analysis has demonstrated additional prognostic value beyond relative perfusion imaging.

A PET Myocardial Perfusion Imaging (MPI) Stress Test consists of intravenous injection of Ru-82 or N-13 labeled ammonia while the heart is at rest. These isotopes have relatively short half-lives (76 seconds and 9.8 minutes respectively). After a few minutes of imaging the heart at rest, the patient is asked to exercise on a treadmill or a stationary cycle. When the heart reaches its peak stress, a second IV injection of the radioactive tracer and a second set of "stress" images are collected by the PET scanner. If a region of the myocardium shows relative lower uptake of radioactivity in the resting image, it may indicate infarct in the myocardium. If the resting image is uniform, but a defect is shown in the "stress" image, it is a sign of ischemia in that region.

Ischemic heart disease (IHD) remains a major healthcare issue in the United States, and often results in myocardial infarction (MI) and adverse post-MI left ventricle (LV) remodeling, which manifests as changes in LV structure, volume, geometry, and function. An estimated eight million people are afflicted with MI in the United States with around 610,000 new cases reported each year.

Significant progress has been made in the development of dynamic positron emission tomography (PET) perfusion imaging to accurately quantify coronary flow reserve, CFR as the ratio of absolute global myocardial blood flow (MBF) measured at peak stress (i.e. during vasodilator induced hyperemia) over that at rest (which is corrected for rate-pressure product as an index of baseline cardiac work). From a pathophysiologic perspective, CFR provides a measure of the integrated effects of epicardial coronary artery disease CAD, diffuse atherosclerosis, vessel remodeling, and microvascular dysfunction on myocardial tissue perfusion.

In contrast to SPECT, PET offers the possibility to routinely quantify perfusion in absolute terms and calculate coronary flow reserve (CFR), which has incremental prognostic value over evaluation of perfusion defects alone. It is demonstrated that a blunted CFR was one of the strongest prognostic factors and trumps clinical risk scores as well as relative perfusion abnormalities.

Conventionally, a cylindrical geometry is the design of choice for a PET scanner. As shown in FIG. 1, the cylindrical geometry can capture all events in the transaxial plane. The axial extent of the detector will determine how many such planes can be defined, as well as how many oblique planes can be utilized.

SUMMARY OF THE INVENTION

A PET scanner is a large scanning machine with a usually round, doughnut shaped hole in the middle, similar to a computed tomography (CT) or magnetic resonance imaging (MRI) unit. Within this PET scanner are multiple detectors that record the annihilation photons emitted from the radiotracer in a patient's body. The present invention relates to an independent vertical-moving horizontal PET detector ring thereby enabling scanning a patient in seated or standing position, and consequently decreasing the footprint of the whole system. This seating position has distinct advantages, particularly in scanning the heart that will be described below.

In order to measure the value of coronary flow reserve (CFR) the PET imaging should starts immediately after the heart reaches its peak stress level. This is not possible if treadmill is used to stress the patient because it takes time for the patient to walk to the PET scanner and be positioned for imaging.

With the present invention of a vertical PET scanner and a stationary cycle for "stressing" the patient while positioned inside the PET detector ring, scanning can start immediately after the heart reaches its peak stress. This allows quantification of myocardial blood flow, as well as the myocardial flow reserve that is important for diagnosis of microvascular disease, a very important issue especially for women.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 3a illustrates the present invention vertical-moving PET scanner with the horizontal aperture detector ring at its highest vertical position for a patient in a wheelchair to be rolled into position for scanning;

FIG. 3b illustrates the present invention vertical-moving PET scanner with the horizontal aperture detector ring being lowered into position for imaging while the patient is sitting in the wheelchair;

FIG. 3c illustrates the present invention vertical-moving PET scanner with the horizontal aperture detector ring in a lower cardiac scanning position while the patient is in the wheelchair;

FIG. 7c illustrates the specialized wheelchair shown in FIG. 7a in a scanning position to be used in conjunction with the present invention vertical-moving PET scanner shown in FIG. 2.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Described briefly, the present invention relates to a vertically-moving horizontal aperture body scanner, so that it's 360° detector ring can be positioned and re-positioned. At the highest position of the detector ring provides an unobstructed path for patient insertion and removal. The detector ring has multiple downward positions which permit sections of 360° scans with multiple slices. Scans could also be sequenced from the bottom position upwards. Vertically seated or standing patients can benefit from analysis of heart and other scanned areas of the body subjected to stress by exercise during, or immediately before scans. The mass of the detector ring and its sensitive sensors and electronics is secured for stable vertical movement by distributed lift mechanisms. There is the added option wherein a patient could be scanned, a procedure performed such as a biopsy, and then scanned to verify the procedure. Other modalities of medical imaging can be performed and the resulting imaging fused to the PET images. Vertical positioning scanning is more compact for a seated or standing patient. Scanning time savings is accomplished by using a specialized wheelchair, because positioning of the patient is done outside the PET scanner and even the initial part of the exercising can happen while another patient is being scanned. By having multiple specialized wheelchairs available, a higher throughput can be achieved in a medical imaging center.

Figure 1:
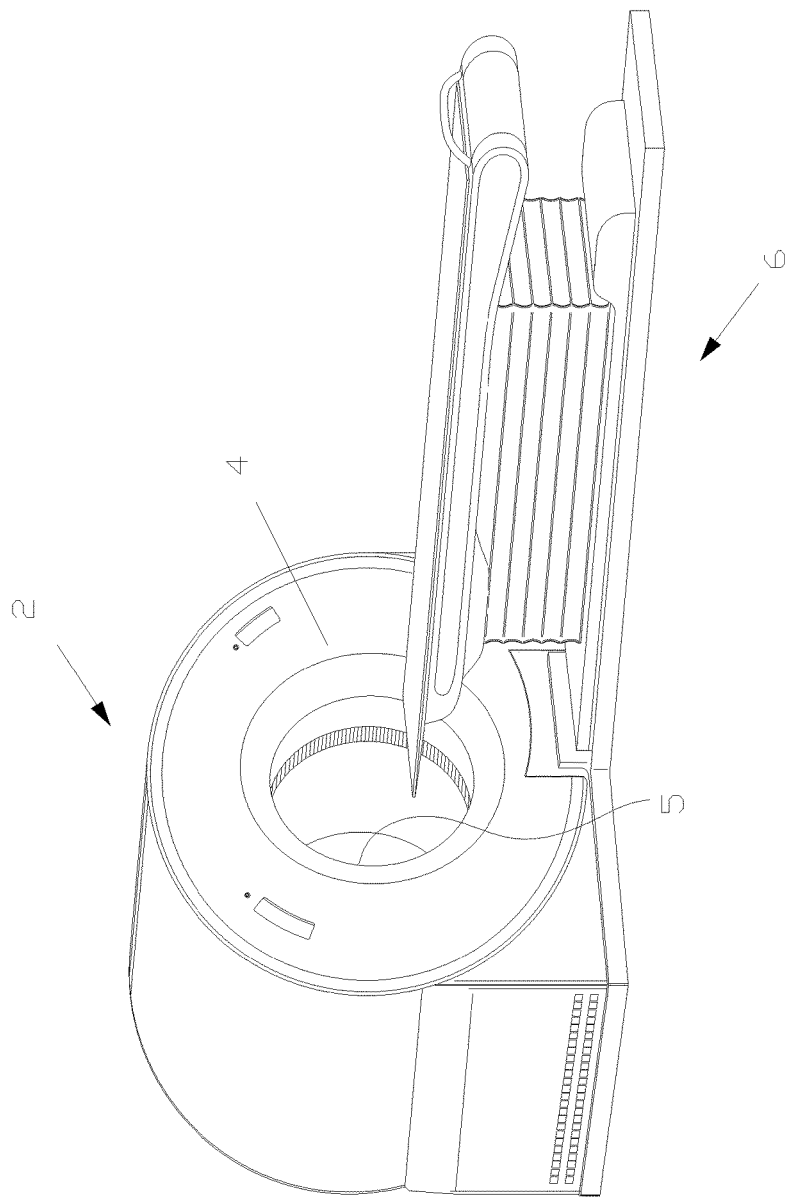
FIG. 1 is a perspective view of a prior art positron emission tomography (PET) scanner with a gantry table.

Referring to FIG. 1, there is shown a prior art positron emission tomography (PET) scanner 2 which comprises a vertical ring detector 4, a gantry table 6, and a computer system (not shown). A support on the gantry table 6 is horizontally moved into the bore 5 of the detector ring 4 in response to commands received from the computer system. The computer system typically includes a display and one or more input devices such as a keyboard or a mouse. Through the keyboard and associated input devices, the operator can control the operation of the PET scanner 2 and the display of the resulting images on the display.

Figure 2:
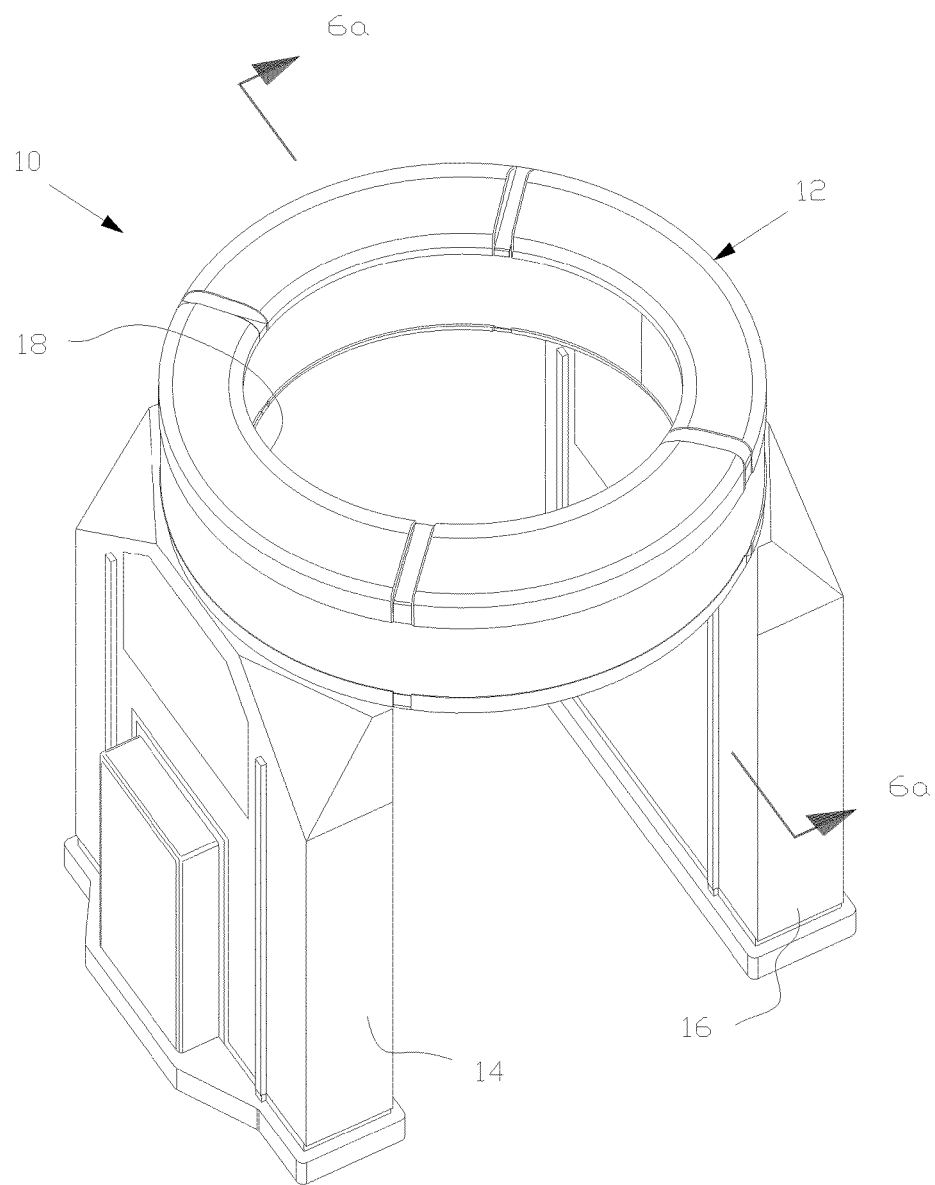
FIG. 2 is a perspective view of the present invention vertical-moving PET scanner with a horizontal aperture detector ring.

Referring to FIG. 2, there is shown the present invention vertical-moving PET scanner 10 which includes a horizontal aperture scan detector ring 12 and two opposite support lifting structures 14 and 16. The scan detector ring 12 has a horizontal aperture 18 which is configured and situated substantially parallel to the floor. The PET scanner 10 is well known and conventional in the art, and the description will not be described in details but will only be described in general terms as the PET scanner 10. The mass of the scan detector ring 12 and its sensitive sensors and electronics is secured for stable vertical movement by distributed support lifting structures 14 and 16.

Referring to FIG. 3a, there is shown the vertical-moving PET scanner 10 with the horizontal aperture 18 detector ring 12 at its highest vertical position for a patient 8 sitting in a specialized wheelchair 110 to be rolled into position for image scanning.

Referring to FIG. 3b, there is shown the vertical-moving PET scanner 10 with the horizontal aperture 18 detector ring 12 being lower while the patient 8 is sitting in the wheelchair 110 to be scanned.

Referring to FIG. 3c, there is shown the vertical-moving PET scanner 10 with the horizontal aperture 18 detector ring 12 in a lower cardiac scan position while the patient 8 is sitting in the wheelchair 110 to be scan.

Figure 4B:
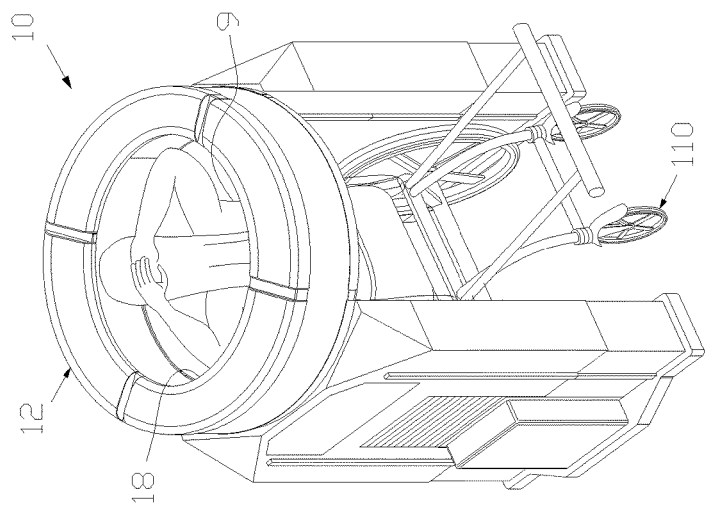
FIG. 4b illustrates the present invention vertical-moving PET scanner with the horizontal aperture detector ring in a raised position to allow a doctor to perform a biopsy on the patient, or other types of imaging (e.g. ultrasound or x-ray mammogram) while sitting in the wheelchair.
Figure 4A:
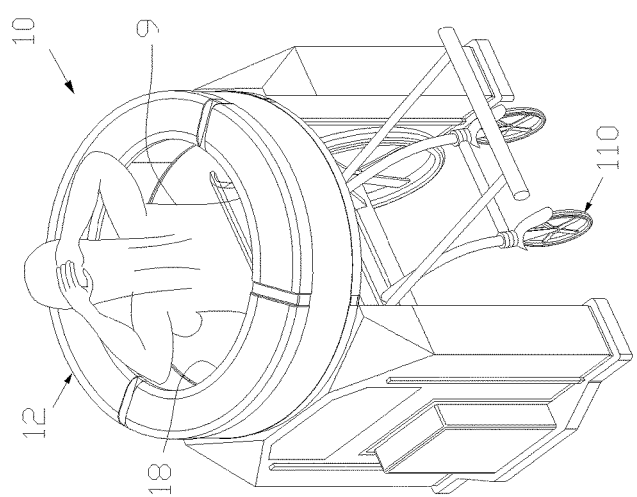
FIG. 4a illustrates the present invention vertical-moving PET scanner with the horizontal aperture detector ring in a lower chest scanning position to scan the breast area of the patient sitting in the wheelchair.

Referring to FIG. 4a, there is shown the vertical-moving PET scanner 10 with the horizontal aperture 18 detector ring 12 in a lower chest scanning position to scan the breast area of the patient 9 sitting in the wheelchair 110.

Referring to FIG. 4b, there is shown the vertical-moving PET scanner 10 with the horizontal aperture 18 detector ring 12 in a raised position to allow a doctor to perform a biopsy, deliver local therapy guided by the PET image, or other imaging procedures on the patient 9 sitting in the wheelchair 110.

Figure 5B:
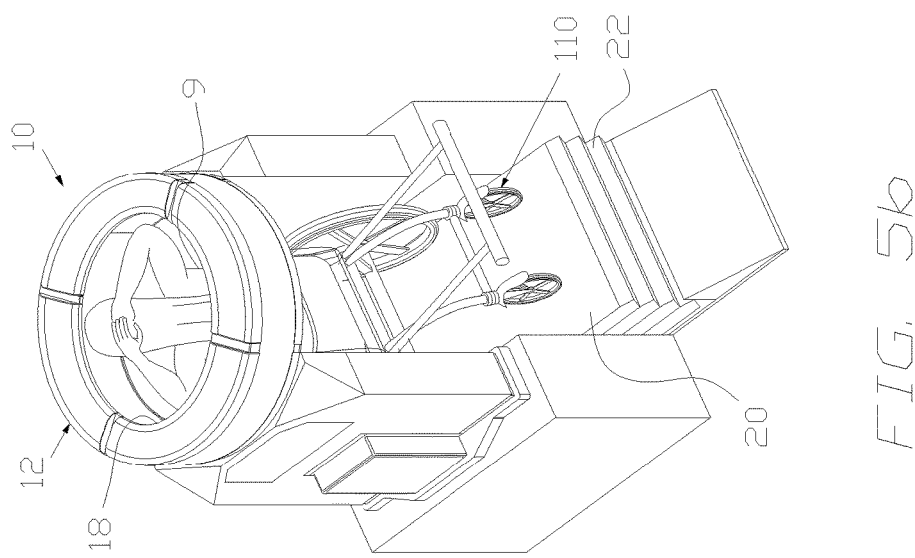
FIGS. 5a and 5b illustrate an alternative embodiment of the present invention PET scanner with a horizontal aperture detector ring situated on a platform, where a patient is sitting in a wheelchair and rolled into a vertical lift to be raised or lowered into position for scanning.
Figure 5A:
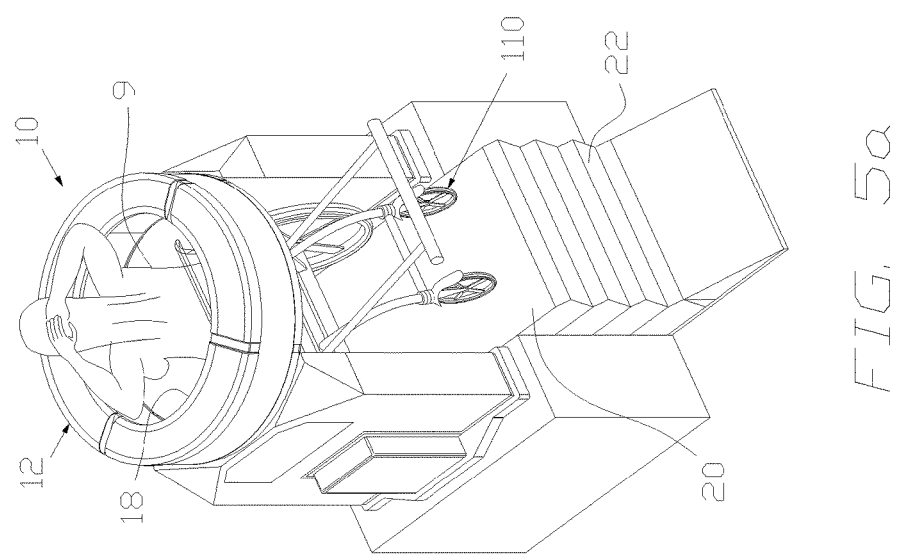

Referring to FIG. 5a, there is shown an alternative embodiment of the vertical-moving PET scanner 10 situated on a platform 20, where a patient 9 is sitting in a wheelchair 110 and rolled into a middle vertical lift 22 and raised into position for PET scanning.

Referring to FIG. 5b, there is shown the alternative embodiment of the vertical-moving PET scanner 10 situated on the platform 20, where the patient 9 is sitting in the wheelchair 110 and rolled into the middle vertical lift 22 for PET scanning.

Figure 6B:
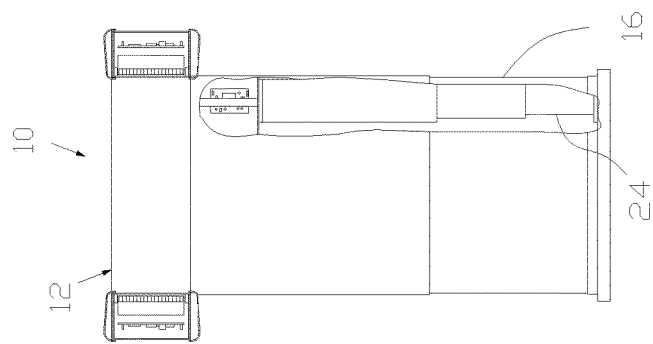
FIG. 6b is a cross sectional view of the present invention vertical-moving PET scanner with the horizontal aperture detector ring at its highest vertical position, showing the basic construction elements.
Figure 6A:
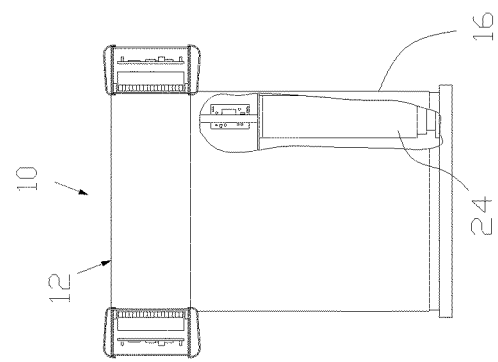
FIG. 6a is a cross sectional view of the present invention vertical-moving PET scanner with the horizontal aperture scan ring at its lowest position, showing the basic construction elements and taken along lines 6a-6a of FIG. 2.

Referring to FIG. 6a, there is shown a cross sectional view taken along lines 6a-6a of the present invention vertical-moving PET scanner 10 with the horizontal aperture detector ring 12 at its lowest position, showing the basic construction elements.

Referring to FIG. 6b, there is shows a cross sectional view of the present invention vertical-moving PET scanner 10 with the horizontal aperture scan ring 12 at its highest vertical position, showing the basic construction elements. Each of the support lifting structures 14 and 16 includes 2 opposite lifting columns 24 which are identical. Each lifting column 24 can be raised or lowered by electrical motor or hydraulic system known in the art. These 4 lifting columns 24 are utilized to distribute the weight of the horizontal aperture detector ring 12 to be raised or lowered by the computer system.

Figure 7B:
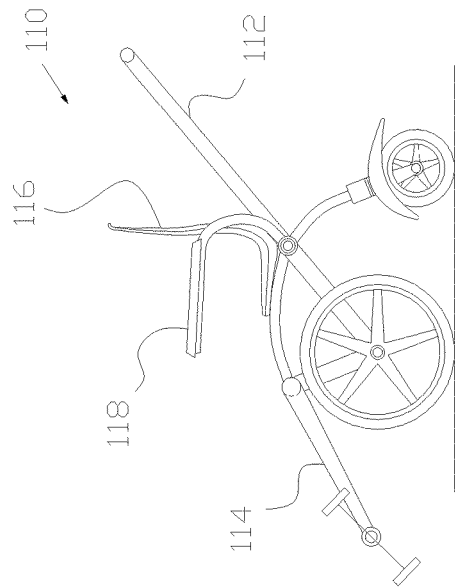
FIG. 7b illustrates the specialized wheelchair shown in FIG. 7a in an exercise position to be used in conjunction with the present invention vertical-moving PET scanner with a horizontal aperture scan ring shown in FIG. 2.
Figure 7A:
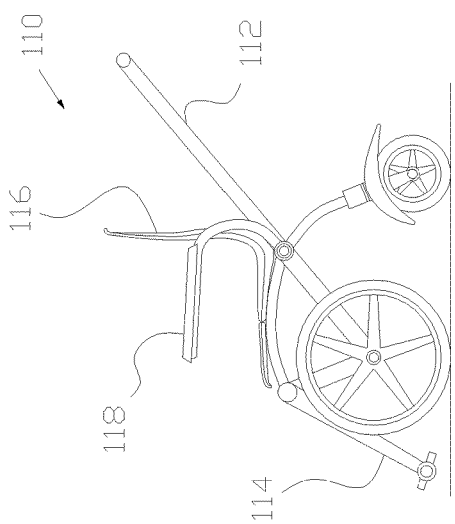
FIG. 7a illustrates a specialized wheelchair for cardiac imaging in a transport position to be used in conjunction with the present invention vertical-moving PET scanner with a horizontal aperture scan ring shown in FIG. 2.

Referring to FIG. 7a, there is shown a specialized wheelchair 110 in a transport position to be used in conjunction with the present invention vertical-moving PET scanner 10 with a horizontal aperture detector ring 12 shown in FIG. 2.

The wheelchair 110 includes a pivot handlebar portion 112, a seat portion 116, a leg portion 114, and an arm portion 118. The handlebar portion 112 and the leg portion 114 are shown in its transport position.

Referring to FIG. 7b, there is shown the specialized wheelchair 110 in its exercise position to be used in conjunction with the present invention vertical-moving PET scanner 10 shown in FIG. 2.

In the exercise position, the leg portion 114 is extended as shown to allow the patient sitting in the wheelchair 110 to exercise.

Referring to FIG. 7c, there is shown the specialized wheelchair 110 in its scanning position to be used in conjunction with the present invention vertical-moving PET scanner 10 shown in FIG. 2.

In the scanning position, the leg portion 114 is positioned downwardly and both the handlebar portion 112 and the arm portion 118 are pivoted down to allow the patient sitting in the seat portion 116 to be scanned together without any issue.

The configuration or placement of the horizontal aperture detector ring 18 can be utilized with other imaging devices, such a computed tomography (CT) unit or a magnetic resonance imaging (MRI) unit or etc.

The present invention can also be a method of scanning a patient's body vertically seated or standing and can benefit from analysis of heart and other scanned areas of the body subjected to stress by exercise during, or immediately before scans.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

The present invention has been described in considerable detail in order to comply with the patent laws by providing full public disclosure of at least one of its forms. However, such detailed description is not intended in any way to limit the broad features or principles of the present invention, or the scope of the patent to be granted. Therefore, the invention is to be limited only by the scope of the appended claims.

What is claimed is:

1. A method for vertically imaging a region of interest of a patient while the patient is sitting or standing within a PET scanning area, the method comprising the steps of:
   providing a horizontal PET scan detector ring having a horizontal aperture, the detector ring having a detector depth of at least six inches and a diameter of at least sixty inches for fully imaging a cross section of significant organ areas of said patient;
   attaching at least three vertical ring columns equally spaced apart from each other at an outer surface of said scan detector ring for providing support and to stabilized image acquisition over the minutes required for scan detector ring;
   providing transport means to transport said patient to said PET scanning area, the transport means having a seat portion, a handlebar portion, an arm portion, and a leg portion where the handlebar portion and the arm portion are pivotable downward to allow the patient sitting in the seat portion to be scanned while in the transport means;
   attaching at least three synchronized motorized devices each respectively to said at least three vertical ring columns for vertically raising said scan detector ring to allow said transport means to enter said PET scanning area in a vertical position and lowering said horizontal aperture of said scan detector ring to scan said region of interest of said patient while said patient is sitting or standing in said transport means and providing vertical precise repeatability imaging so that multiple cross sections are aligned within a software; and
   controlling said horizontal aperture of said scan detector ring to scan said patient vertical cross sections which are horizontally flat with repeatable horizontal image planes so that multiple cross sections are aligned while said patient is sitting or standing within said scanning area of said detector ring.

2. The method in accordance with claim 1 wherein said at least three synchronized motorized devices are electrical motors.

3. The method in accordance with claim 1 wherein said at least three synchronized motorized devices are hydraulic.

4. The method in accordance with claim 1 wherein said seat portion is made out of scannable material.

5. The method in accordance with claim 1 wherein said controlling said horizontal aperture of said scan detector ring includes a computer system.

6. A PET imaging scanner for vertically imaging a region of interest of a patient within a scanning area, the PET imaging scanner comprising:
   a horizontal scan detector ring having a horizontal aperture, the detector ring having a detector depth of at least six inches and a diameter of at least sixty inches for fully imaging a cross section of significant organ areas of said patient;
   at least three vertical ring columns equally spaced apart from each other and attached to an outer surface of said scan detector ring for providing support and to stabilized image acquisition over the minutes required for said PET imaging scanner;
   at least three synchronized motorized devices each respectively attached to said at least three vertical ring columns for providing vertical precise repeatability imaging so that multiple cross sections are aligned within a software; and
   a computer system for controlling a vertical scanning of said organ areas of said patient within said horizontal aperture of said scan detector ring while said patient is sitting or standing within said horizontal aperture.

7. The PET imaging scanner in accordance with claim 6 wherein said at least three synchronized motorized devices includes electrical motors.

8. The PET imaging scanner in accordance with claim 6 wherein said at least three synchronized motorized devices includes hydraulic.

9. A PET imaging scanner for vertically imaging a region of interest of a patient within a scanning area, the PET imaging scanner comprising:
   a horizontal scan detector ring having a horizontal aperture, the detector ring having a detector depth of at least six inches and a diameter of at least sixty inches for fully imaging a cross section of significant organ areas of said patient;
   four vertical ring columns equally spaced apart from each other and attached to an outer surface of said scan detector ring for providing support and to stabilized image acquisition over the minutes required for said PET imaging scanner;
   four synchronized motorized devices each respectively attached to said four vertical ring columns for providing vertical precise repeatability imaging so that multiple cross sections are aligned within a software; and
   a computer system for controlling a vertical scanning of said organ areas of said patient within said horizontal aperture of said scan detector ring while said patient is sitting or standing within said horizontal aperture.

10. The PET imaging scanner in accordance with claim 9 wherein said four synchronized motorized devices includes electrical motors.

11. The PET imaging scanner in accordance with claim 9 wherein said four synchronized motorized devices includes hydraulic.

\* \* \* \* \*